(12) United States Patent
Daly et al.

(10) Patent No.: US 6,313,068 B1
(45) Date of Patent: Nov. 6, 2001

(54) SYNTHESIS METHODS, COMPLEXES AND DELIVERY METHODS FOR THE SAFE AND CONVENIENT STORAGE, TRANSPORT AND APPLICATION OF COMPOUNDS FOR INHIBITING THE ETHYLENE RESPONSE IN PLANTS

(75) Inventors: James Daly; Bob Kourelis, both of Chicago, IL (US)

(73) Assignee: AgroFresh, Inc., Philadelphia, PA (US)

( * ) Notice: Subject to any disclaimer, the term of this patent is extended or adjusted under 35 U.S.C. 154(b) by 0 days.

(21) Appl. No.: 09/367,654

(22) Filed: Aug. 20, 1999

Related U.S. Application Data

(63) Continuation-in-part of application No. 09/137,056, filed on Aug. 20, 1998, now Pat. No. 6,017,849.

(51) Int. Cl.[7] ............................. A01N 3/02; A01N 37/00; A01N 31/00; C07C 13/00; C07C 5/31

(52) U.S. Cl. ........................ 504/114; 504/115; 504/320; 504/326; 504/353; 504/356; 585/23; 585/365; 585/379; 585/380

(58) Field of Search ............................ 504/114, 115, 504/320, 326, 353, 356; 585/23, 365, 379, 380

(56) References Cited

U.S. PATENT DOCUMENTS 5,518,988 * 5/1996 Sisler et al. .................... 504/114

\* cited by examiner

*Primary Examiner*—Deborah C. Lambkin
(74) *Attorney, Agent, or Firm*—Sonnenschein Nath & Rosenthal

(57) ABSTRACT

The present invention generally relates to the regulation of plant physiology, in particular to methods for inhibiting the ethylene response in plants or plant products, and has three embodiments. The first embodiment relates to methods of minimizing impurities capable of reversibly binding to plant ethylene receptor sites during the synthesis of cyclopropene and its derivatives such as methylcyclopropene, thereby avoiding the negative effects these impurities have on plants treated with cyclopropene and its derivatives. The second embodiment relates to complexes formed from molecular encapsulation agents such as cyclodextrin, and cyclopropene and its derivatives such as methylcyclopropene, in addition to cyclopentadiene and diazocyclopentadiene and their derivatives, thereby providing a convenient means for storing and transporting these compounds capable of inhibiting the ethylene response in plants, which are reactive gases and highly unstable because of oxidation and other potential reactions. The third embodiment relates to convenient methods of delivering to plants these compounds capable of inhibiting the ethylene response in the plants in order to extend their shelf life.

19 Claims, No Drawings

US 6,313,068 B1

SYNTHESIS METHODS, COMPLEXES AND DELIVERY METHODS FOR THE SAFE AND CONVENIENT STORAGE, TRANSPORT AND APPLICATION OF COMPOUNDS FOR INHIBITING THE ETHYLENE RESPONSE IN PLANTS

This application is a continuation-in-part of application Ser. No. 09/137,056, filed on Aug. 20, 1998, now U.S. Pat. No. 6,017,849.

FIELD OF THE INVENTION

The present invention generally relates to the regulation of plant physiology, in particular to methods for inhibiting the ethylene response in plants or plant products, in order to prolong their shelf life. The invention relates to prolonging the shelf life of cut flowers and ornamentals, potted plants (edible and non-edible), transplants, and plant foods including fruits, vegetables and root crops.

The present invention has three embodiments. The first embodiment relates to methods of minimizing impurities capable of reversibly binding to plant ethylene receptor sites during the synthesis of cyclopropene and its derivatives, in particular methylcyclopropene. Certain impurities produced during the manufacture of cyclopropene and its derivatives, in particular methylcyclopropene, have negative effects on treated plants. Therefore, when plants are treated with cyclopropene and its derivatives, in particular methylcyclopropene, made by using the methods of synthesis of the present invention, the negative effects of these impurities are avoided.

The second embodiment of the present invention relates to complexes formed from molecular encapsulation agents, such as cyclodextrin, and cyclopropene or its derivatives, such as methylcyclopropene, in addition to complexes formed from molecular encapsulation agents and cyclopentadiene or diazocyclopentadiene or their derivatives. These molecular encapsulation agent complexes provide a convenient and safe means for storing and transporting the compounds capable of inhibiting the ethylene response in plants. These molecular encapsulation agent complexes are important because the compounds capable of inhibiting the ethylene response in plants are reactive gases and therefore highly unstable because of oxidation and other potential reactions.

The third embodiment relates to convenient methods of delivering to plants the compounds capable of inhibiting their ethylene responses in order to extend shelf life. These methods involve contacting the molecular encapsulation agent complex with a solvent capable of dissolving the molecular encapsulation agent, thereby liberating the compound capable of inhibiting the ethylene response so it can contact the plant.

BACKGROUND OF THE INVENTION

The present invention generally relates to the regulation of plant growth and to methods of inhibiting ethylene responses in plants by application of cyclopropene, cyclopentadiene, diazocyclopentadiene or their derivatives, in particular methylcyclopropene. The present invention specifically relates to methods of synthesis and molecular encapsulation agent complexes, in addition to storage, transport and application of these gases that inhibit ethylene responses in plants.

Plant growth responses are affected by both internal and external factors. Internal control of plant processes are under the influence of genetic expression of the biological clocks of the plant. These processes influence both the extent and timing of growth processes. Such responses are mediated by signals of various types which are transmitted within and between cells. Intracellular communication in plants typically occurs via hormones (or chemical messengers) as well as other less understood processes.

Because communications in a plant are typically mediated by plant hormones, both the presence and levels of such hormones are important to specific plant cell reactions. The plant hormone that is most relevant to the present invention is ethylene, which has the capacity to affect many important aspects of plant growth, development and senescence. The most important effects of ethylene include processes normally associated with senescence, particularly fruit ripening, flower fading and leaf abscission.

It is well known that ethylene can cause the premature death of plants including flowers, leaves, fruits and vegetables. It can also promote leaf yellowing and stunted growth as well as premature fruit, flower and leaf drop.

Because of these ethylene-induced problems, very active and intense research presently concerns the investigation of ways to prevent or reduce the deleterious effects of ethylene on plants.

One major type of treatment used to mitigate the effects of ethylene employs ethylene synthesis inhibitors. These ethylene synthesis inhibitors reduce the quantity of ethylene that a plant can produce. Specifically, these ethylene synthesis inhibitors inhibit pyridoxal phosphate-mediated reactions and thereby prevent the transformation of S-adenosynimethione to 1-amino cyclopropane-1-carboxylic acid, the precursor to ethylene. Staby et al. ("Efficacies of Commercial Anti-ethylene Products for Fresh Cut Flowers", Hort Technology, pp. 199–202, 1993) discuss the limitations of these ethylene synthesis inhibitors. Because ethylene synthesis inhibitors only inhibit a treated plant's production of ethylene, they do not suppress the negative effects of ethylene from environmental sources. These environment sources of ethylene exist because ethylene is also produced by other crops, truck exhaust, ethylene gashing units and other sources, all of which can affect a plant during production, shipment, distribution and end use. Because of this, ethylene synthesis inhibitors are less effective than products that thwart a plant's ethylene responses. For a discussion of the ethylene response in plants, see U.S. Pat. No. 3,879,188.

The other major type of treatment used to mitigate the effects of ethylene employs blocking the receptor site that signals ethylene action. One of the best known compounds for inhibiting the ethylene response in plants, as well as preventing the deleterious effects from environmental sources of ethylene, is silver thiosulfate ("STS"). An example of a commercial STS product is SILFLOR solution, available from Floralife, Inc., Burr Ridge, Ill. STS is very effective in inhibiting the ethylene response in plants and has been used because it moves easily in the plant and is not toxic to plants in its effective concentration range. STS can be used by growers, retailers and wholesalers as a liquid that is absorbed into the stems of the flowers. While STS is highly effective, it has a serious waste disposal problem. It is illegal to dispose of the silver component of STS by conventional means, such as by using a laboratory sink, without first pretreating the STS to remove the silver. It is also illegal to spray STS on potted plants. Consequently because of this disposal problem which is typically ignored by growers, STS is now almost exclusively utilized only by growers. Therefore, there is a great desire among postharvest physiologists to find alternatives to STS. To the knowledge of the present inventors, the only commercially acceptable replacements for STS are cyclopropene, cyclopentadiene, diazocyclopentadiene and their derivatives.

Many compounds such as carbon dioxide which block the action of ethylene diffuse from the ethylene receptor or binding site over a period of a few hours. Sisler & Wood, Plant Growth Reg. 7, 181–191, 1988. While these compounds may be used to inhibit the action of ethylene, their effect is reversible and therefore they must be exposed to the plant in a continuous manner if the ethylene inhibition effect is to last for more than a few hours. Therefore, an effective agent for inhibiting the ethylene response in plants should provide an irreversible blocking of the ethylene binding sites and thereby allow treatments to be of short duration.

An example of an irreversible ethylene inhibiting agent is disclosed in U.S. Pat. No. 5,100,462. However, the diazocyclopentadiene described in that patent is unstable and has a strong odor. Sisler et al., Plant Growth Reg. 9, 157–164, 1990, showed in a preliminary study that cyclopentadiene was an effective blocking agent for ethylene binding. However, the cyclopentadiene described in that reference is also unstable and has a strong odor.

U.S. Pat. No. 5,518,988 discloses the use of cyclopropene and its derivatives, including methylcyclopropene, as effective blocking agents for ethylene binding. Although the compounds in this patent do not suffer from the odor problems of diazocyclopentadiene and cyclopentadiene, because they contain a carbene group, they are relatively unstable due to their potential for undergoing oxidation and other reactions. Therefore, a problem of stability of these gases, as well as the explosive hazards these gases present when compressed, exist. To solve these problems, the present inventors have developed a method of incorporating these gaseous compounds, which inhibit the ethylene response in plants, in a molecular encapsulation agent complex in order to stabilize their reactivity and thereby provide a convenient and safe means of storing, transporting and applying or delivering the active compounds to plants. The application or delivery methods of these active compounds can be accomplished by simply adding water to the molecular encapsulation agent complex.

In trying to implement the teaching of U.S. Pat. No. 5,518,988, the problems associated with the stability of the gases and the potential explosive hazard of using compressed gases limit their use and therefore their effectiveness. To solve those problems, the present inventors developed a molecular encapsulation agent complex that stabilizes the reactivity of these gases and thereby provides a convenient and safe means of storing, transporting and applying or delivering these gases to plants.

This approach is an important advance over the art as it allows for the convenient and safe storage, transport and use of gases that are otherwise difficult to store, ship and dispense. The present invention will now allow for the safe, convenient and consistent use of these gases in the field by the grower, in addition to their use in distribution and in the retail marketplace. In fact, a complex of methylcyclopropene and the molecular encapsulating agent cycloclextrin allows for a product having a shelf life of greater than one year.

Another feature of the molecular encapsulation agents of the present invention is that once they trap the gaseous active agent in the complex, the complex (and hence the gaseous active agent) does not exhibit a very high vapor pressure and is therefore protected from oxidation and other chemical degradation reactions. A gaseous active compound such as cyclopropene or derivatives thereof is held in a caged molecule whereby the vapor pressure of the solid is very low due to the weak atomic forces (van de Waals and hydrogen binding). The binding of these gaseous active compounds with these molecular encapsulation agents holds the active compound until ready for use.

The present invention also prolongs the life of plants by providing an effective and proper dose of the encapsulated active compound capable of inhibiting the ethylene response, which is subsequently desorbed into a gas form for administration to the plant. The invention further embodies the release of the desired active compound from the complex by dissolving the complex in a suitable solvent in order to release the gaseous active compound, thereby serving as an improved gaseous plant treatment.

A major advantage of the present invention is that it provides an effective, user-friendly product for non-technical customers, florists and wholesalers. In addition, the molecular encapsulation agent complex acts as a controlled release agent for treatment with such active gaseous compounds as cyclopropene and methylcyclopropene. As a result, the present invention promotes less human exposure to the target compound than other means of application. Additionally, the user has more control over the application of the gaseous active compound because the active gaseous compound is slowly released from the complex in the presence of a suitable solvent.

Another advantage of the present invention is the amount of selective inclusion of the gaseous active compounds such as cyclopropene and methylcyclopropene into the molecular encapsulation agent. Using the teachings of the present invention, significant quantities of methylcyclopropene and other active compounds can now be encapsulated into a molecular encapsulation agent such as cyclodextrin, far exceeding the normal expected amount usually found with other solids.

A still further advantage of the present invention over the use of compressed concentrated gases is the elimination of the need for gas tanks, regulators, and OSHA compliance for pressurized gas tanks. This results in a substantial cost savings for the manufacturer as well as the customer. In addition, it eliminates the explosive and flammable potential associated with the use of gas tanks holding a highly reactive organic molecule. Moreover, the present invention eliminates the self polymerization and decomposition of gases that occur with compressed gases or liquids containing them.

Another advantage of the present invention over other inert solid carrier systems proposed for use in applying cyclopropene, such as dust, talc, silica and flour, is that it provides a product containing the active gaseous compound with increased stability. For example, the molecular encapsulation agent cyclodextrin protects the active cyclopropene or methylcyclopropene molecule from external conditions, such as ultraviolet degradation, which are problematic in photosensitive compounds such as these.

A still further advantage of the present invention is that the molecular encapsulation agent complex results in more effective use of the active gaseous compound. For example, a reduced quantity of cyclopropene can be utilized to obtain an effective treatment compared with the use of prior proposed cyclopropene solid carriers or compressed gases. This results in less waste and less packaging needed for the commercial product.

In another embodiment, this invention relates to the synthesis of cyclopropene and its derivatives including methylcyclopropene by methods that lower the incidence of impurities, such as hazardous reaction products and by-products, that interfere with the ethylene binding effectiveness of cyclopropene and its derivatives. These reaction product impurities include compounds that bind tightly but reversibly to the ethylene receptor site and inhibit the irreversible binding of cyclopropene and its derivatives, especially methylcyclopropene. The synthesis of these cyclopropene and derivative compounds is important because if irreversible binding to the receptor site does not take place during plant treatment, the plant will not be protected against the effects of ethylene.

The prior art syntheses of methylcyclopropene has created problems when the methylcyclopropene was used for inhibiting the ethylene response in plants. While it is well documented in U.S. Pat. No. 5,518,988 that methylcyclopropene and other similar compounds are active against ethylene, it has been discovered that not all methods of synthesis are as effective or preferable as the presently claimed synthesis method.

First, it is necessary to avoid producing during synthesis products (or impurities) that reversibly bind to the same ethylene receptor site as the intended active compound. Because these impurities do not irreversibly bind in a manner consistent with the inactivation of the receptor site without phytotoxicity, the effectiveness of using such a reaction product mixture without further processing is reduced. The specific impurities that must be avoided in the synthesis in order to obtain optimal performance of the reaction mixture include methylenecyclopropane, methylcyclopropanes and butanes.

The present inventors have discovered that of all the Lewis bases used for the production of methylcyclopropene, sodium amide and lithium diisopropylamide are most preferred. Synthesis using various metal hydrides and hydroxides were found to produce high levels of other reaction products that lowered the performance of the methylcyclopropene for plant uses. For example, using butynes, 3-hydroxy-2-methylpropenes and other similar starting materials generally yields an impure reaction product that is not appropriate for use in the treatment of plants.

Additional features and advantages of the present invention are described in, and will be apparent from, the detailed description and examples provided.

SUMMARY OF THE INVENTION

In a method of minimizing impurities embodiment, the present invention relates to a method of minimizing impurities capable of reversibly binding to plant ethylene receptor sites comprising the steps of reacting, in an inert environment, a metal amide salt and a halogenated carbene, optionally in the presence of a non-reactive solvent, to form a compound having the following structure

wherein n is a number from 1 to 10 and R is selected from the group consisting of hydrogen, saturated or unsaturated C1 to C10 alkyl, hydroxy, halogen, C1 to C10 alkoxy, amino and carboxy. This method of minimizing impurities embodiment is generically referred to as the cyclopropene method of minimizing impurities. The preferred metal amide salts for use in this method of minimizing impurities embodiment are sodium amide, lithium amide, potassium amide, lithium diisopropylamide and sodium diisopropylamide. The preferred halogenated carbenes for use in this method of minimizing impurities embodiment are 3-chloro-3-methyl-2-methylpropene, 3-bromo-3-methyl-2-methylpropene, 3-chloro-2-methylpropene and 3-bromo-2-methylpropene.

In a more specific method of minimizing impurities embodiment, the present invention relates to a method of minimizing impurities capable of reversibly binding to plant ethylene receptor sites comprising the steps of reacting, in an inert environment, a metal amide salt and a halogenated methyl propene, optionally in the presence of a non-reactive solvent, to form methylcyclopropene. This more specific method of minimizing impurities embodiment is referred to as the methylcyclopropene method of minimizing impurities. The preferred metal amide salts for use in this more specific method of minimizing impurities embodiment are sodium amide, lithium amide, potassium amide, lithium diisopropylamide and sodium diisopropylamide. The preferred halogenated methyl propenes for use in this more specific method of minimizing impurities embodiment are 3-chloro-2-methylpropene and 3-bromo-2-methylpropene.

In one of the molecular encapsulation agent complex embodiments, which is generically referred to as the cyclopropene molecular encapsulation agent complex, the complex is formed from a molecular encapsulation agent and a compound having the following structure

wherein n is a number from 1 to 10 and R is selected from the group consisting of hydrogen, saturated or unsaturated C1 to C10 alkyl, hydroxy, halogen, C1 to C10 alkoxy, amino and carboxy. The preferred molecular encapsulation agents for use in this cyclopropene molecular encapsulation agent complex embodiment include a cyclodextrin, a crown ether, a polyoxyalkylene, a prophorine, a polysiloxane, a phopnazene and a zeolite. Cyclodextrin and in particular alpha-cyclodextrin are particularly preferred. The preferred compounds capable of inhibiting the ethylene response in plants for use in this cyclopropene molecular encapsulation agent complex embodiment are cyclopropene and dimethylcyclopropene.

In a more specific molecular encapsulation agent complex embodiment, which is referred to as the methylcyclopropene molecular encapsulation agent complex, the complex is formed from a nolecular encapsulation agent and methylcyclopropene. The preferred molecular encapsulation agents for use in this methylcyclopropene molecular encapsulation agent complex embodiment include a cyclodextrin, a crown ether, a polyoxyalkylene, a prophorine, a polysiloxane, a phophazene and a zeolite. Cyclodextrin and in particular alpha-cyclodextrin are particularly preferred.

In another molecular encapsulation agent complex embodiment, which is generically referred to as the cyclopentadiene molecular encapsulation agent complex, the complex is formed from a molecular encapsulation agent and a compound having the following structure

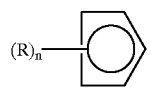

wherein n is a number from 1 to 10 and R is selected from the group consisting of hydrogen, saturated or unsaturated C1 to C10 alkyl, hydroxy, halogen, C1 to C10 alkoxy, amino and carboxy. The preferred molecular encapsulation agents for use in this cyclopentadiene molecular encapsulation agent complex embodiment include a cyclodextrin, a crown ether, a polyoxyalkylene, a prophorine, a polysiloxane, a phophazene and a zeolite. Cyclodextrin and in particular alpha-cyclodextrin are particularly preferred.

In still another molecular encapsulation agent complex embodiment, which is generically referred to as the diazocyclopentadiene molecular encapsulation agent complex, the complex is formed from a molecular encapsulation agent and a compound having the following structure $$(R)_n \text{—} \bigcirc \text{—} N \equiv N$$

wherein n is a number from 1 to 10 and R is selected from the group consisting of hydrogen, saturated or unsaturated C1 to C10 alkyl, hydroxy, halogen, C1 to C10 alkoxy, amino and carboxy. The preferred molecular encapsulation agents for use in this diazocyclopentadiene molecular encapsulation agent complex embodiment include a cyclodextrin, a crown ether, a polyoxyalkylene, a prophorine, a polysiloxane, a phophazene and a zeolite. Cyclodextrin and in particular alpha-cyclodextrin are particularly preferred.

In one of the method of delivery of a compound to a plant to inhibit an ethylene response in the plant embodiments, which is generically referred to as the cyclopropene method of delivery, the method comprises the step of contacting a complex formed from a molecular encapsulation agent and a compound having the following structure $$(R)_n \text{—} \triangle$$

wherein n is a number from 1 to 10 and R is selected from the group consisting of hydrogen, saturated or unsaturated C1 to C10 alkyl, hydroxy, halogen, C1 to C10 alkoxy, amino and carboxy, with a solvent capable of dissolving the molecular encapsulation agent, and thereby liberating the compound from the molecular encapsulation agent so that it can contact the plant. The preferred molecular encapsulation agents for use in this cyclopropene method of delivery embodiment include a cyclodextrin, a crown ether, a polyoxyalkylene, a prophorine, a polysiloxane, a phophazene and a zeolite. Cyclodextrin and in particular alpha-cyclodextrin are particularly preferred. The preferred compounds capable of inhibiting the ethylene response in plants for use in this cyclopropene method of delivery embodiment are cyclopropene and dimethylcyclopropene. The preferred solvent for use in this cyclopropene method of delivery embodiment is water, and the water may additionally comprise an acidic or alkaline agent. A more specific feature of this cyclopropene method of delivery embodiment comprises bubbling a gas through the solvent while it is in contact with the complex. In addition, another specific feature of this cyclopropene method of delivery embodiment comprises applying heat to the solvent either before it contacts the complex or during that contact.

In a more specific method of delivery embodiment, which is specifically referred to as the methylcyclopropene method of delivery, the method comprises the step of contacting a complex formed between a molecular encapsulation agent and methylcyclopropene with a solvent capable of dissolving the molecular encapsulation agent, and thereby liberating the methylcyclopropene from the molecular encapsulation agent so that it can contact the plant. The preferred molecular encapsulation agents for use in this methylcyclopropene method of delivery embodiment include a cyclodextrin, a crown ether, a polyoxyalkylene, a prophorine, a polysiloxane, a phophazene and a zeolite. Cyclodextrin and in particular alpha-cyclodextrin are particularly preferred. The preferred solvent for use in this methylcyclopropene method of delivery embodiment is water, and the water may additionally comprise an acidic or alkaline agent. For example, a buffering solution that can be used to facilitate the release of the methylcyclopropene gas contains 0.75% potassium hydroxide and 0.75% sodium hydroxide after the proper amount of water is added. A more specific feature of this methylcyclopropene method of delivery embodiment comprises bubbling a gas through the solvent while it is in contact with the complex. In addition, another specific feature of this methylcyclopropene method of delivery embodiment comprises applying heat to the solvent either before it contacts the complex or during that contact.

In another method of delivery embodiment, which is generically referred to as the cyclopentadiene method of delivery, the method comprises the step of contacting a complex formed from a molecular encapsulation agent and a compound having the following structure $$(R)_n \text{—} \bigcirc$$

wherein n is a number from 1 to 10 and R is selected from the group consisting of hydrogen, saturated or unsaturated C1 to C10 alkyl, hydroxy, halogen, C1 to C10 alkoxy, amino and carboxy, with a solvent capable of dissolving the molecular encapsulation agent, and thereby liberating the compound from the molecular encapsulation agent so that it can contact the plant. The preferred molecular encapsulation agents for use in this cyclopentadiene method of delivery embodiment include a cyclodextrin, a crown ether, a polyoxyalkylene, a prophorine, a polysiloxane, a phophazene and a zeolite. Cyclodextrin and in particular alpha-cyclodextrin are particularly preferred. The preferred solvent for use in this cyclopentadiene method of delivery embodiment is water, and the water may additionally comprise an acidic or alkaline agent. A more specific feature of this cyclopentadiene method of delivery embodiment comprises bubbling a gas through the solvent while it is in contact with the complex. In addition, another specific feature of this cyclopentadiene method of delivery embodiment comprises applying heat to the solvent either before it contacts the complex or during that contact.

In still another method of delivery embodiment, which is generically referred to as the diazocyclopentadiene method of delivery, the method comprises the step of contacting a complex formed from a molecular encapsulation agent and a compound having the following structure $$(R)_n \text{—} \bigcirc \text{—} N \equiv N$$

wherein n is a number from 1 to 10 and R is selected from the group consisting of hydrogen, saturated or unsaturated C1 to C10 alkyl, hydroxy, halogen, C1 to C10 alkoxy, amino and carboxy, with a solvent capable of dissolving the molecular encapsulation agent, and thereby liberating the compound from the molecular encapsulation agent so that it can contact the plant. The preferred molecular encapsulation agents for use in this diazocyclopentadiene method of delivery embodiment include a cyclodextrin, a crown ether, a polyoxyalkylene, a prophorine, a polysiloxane, a phophazene and a zeolite. Cyclodextrin and in particular alpha-cyclodextrin are particularly preferred. The preferred solvent for use in this diazocyclopentadiene method of delivery embodiment is water, and the water may additionally comprise an acidic or alkaline agent. A more specific feature of this diazocyclopentadiene method of delivery embodiment comprises bubbling a gas through the solvent while it is in contact with the complex. In addition, another specific feature of this diazocyclopentadiene method of delivery embodiment comprises applying heat to the solvent either before it contacts the complex or during that contact.

DETAILED DESCRIPTION OF THE INVENTION

The Compounds that Inhibit Plant Ethylene Responses

The compounds that inhibit ethylene responses in plants are disclosed in the following references, all of which are incorporated by reference. U.S. Pat. No. 5,100,462 discloses that diazocyclopentadiene and its derivatives are effective blocking agents that inhibit the ethylene response in plants. Sisler et al., Plant Growth Reg. 9, 157–164, 1990, discloses that cyclopentadiene was an effective blocking agent for inhibiting the ethylene response in plants. U.S. Pat. No. 5,518,988 discloses that cyclopropene and its derivatives, including methylcyclopropene, are effective blocking agents for inhibiting the ethylene response in plants. Rather than repeat the disclosure of those references in this specification, they are incorporated by reference in their entireties.

The derivatives of cyclopropene, cyclopentadiene and diazocyclopentadiene may contain from 1 to 4 R groups. The number of such R groups is more preferably 2 and most preferably 1. As previously mentioned, suitable R groups include hydrogen, saturated or unsaturated C1 to C10 alkyl, hydroxy, halogen, C1 to C10 alkoxy, amino and carboxy.

The term "alkyl" is defined herein to refer to linear or branched, saturated or unsaturated alkyl groups. Examples include but are not limited to methyl, ethyl, propyl, isopropyl and butyl. Alkyl groups of the present invention are most preferably single carbon or linear.

The Synthesis of the Cyclopropene and Methylcyclopropene Embodiments

Pursuant to the present invention, cyclopropene and its derivatives are made by reacting, in an inert environment, a metal amide salt, such as lithium amide salt, sodium amide salt, potassium amide salt, lithium diisopropylamide salt, sodium diisopropylamide salt or other metal amide salts, and a halogenated carbene, such as 3-chloro-3-methyl-2-methylpropene, 3-bromo-3-methyl-2-methylpropene, 3-chloro-2-methylpropene, 3-bromo-2-methylpropene or some other halogenated carbene. The specific compounds named above are preferred. Methylcyclopropene is made under the same conditions with the same metal amide salts discussed above by reacting them with a halogenated methylpropene. The preferred halogenated methyl propenes are 3-chloro-2-methylpropene and 3-bomo-2-methylpropene. These halogenated methyl propenes lead to a high purity product for the intended use and are readily available.

Suitable methods for making cyclopropene and its derivatives, including methylcyclopropene, are covered in the examples below. While a variety of different volatile and non-volatile non-reactive solvents can be utilized, preferred suitable solvents include glycerine, mineral oil, polyethylene glycol, diglyme and tetraglyme. The use of a non-reactive solvent is optional. The inert environment can be created by any known method including purging the reaction vessel with nitrogen or any other inert gas. The concentration ratio of the metal amide salt to the halogenated carbene or halogenated methyl propene is a molar ratio of about 1:1 to about 4:1. The reaction temperature can range from about 20° to about 60° C. and the reaction pressure can range from about 1 to about 100 psi.

The resulting exothermic solution from this reaction is allowed to react until no further heat is given off. After the reaction is complete, a polar solvent is added to the reaction solution. While a variety of polar solvents can be used, suitable examples of such polar solvents include water, acetone and alcohol. After the polar solvent has been added, the head space of the reaction solution is displaced, cooled and placed into a second vessel containing a molecular encapsulation agent, such as cyclodextrin, and buffered water to form the desired molecular encapsulation agent complex.

When the gas is released into the original vessel using sodium amide, a non-polar solvent is used to release the gas when a lithium salt is employed as the metal amide salt.

Although it is not necessary to achieve the objectives of this invention, fractional distillation can be used on the final product.

In one preferred embodiment, the headspace of the reaction solution is cooled through a condenser and cold trap. The water used with the molecular encapsulation agent is buffered to approximately a pH of 4 to 6, and the reaction product and molecular encapsulation agent is stirred for 1 to 24 hours at temperatures ranging from room temperature to 40° C. After the complex is formed, the excess water is filtered off and the resulting slurry dried to form a powder. The examples below describe a method of preparing a molecular encapsulation agent from methylcyclopropene and alpha-cyclodextrin.

The Molecular Encapsulation Agent Complex

As previously explained, forming a complex from the molecular encapsulation agent and the gaseous compound capable of inhibiting the ethylene response in plants is important for two reasons. First, strained carbenes such as methylcyclopropene are quite unstable to reaction with oxygen, self polymerization and reaction with other organic compounds. The complexes of the present invention overcome those instability problems. Second, it is preferable to use a product that has a long shelf life, is simple to handle and comparatively non-reactive. The complexes of the present invention meet those objectives as well.

Methylcyclopropene is reactive and explosive at concentrations over one percent. Additionally, it is difficult to handle as a gas, requires compression into metal containers or the use of a non-oxygen permeable container. Since for most applications, less than 1 ppm (part per million) and preferably less than 1 ppb (parts per billion) of methyloyclopropene in the atmosphere are required, the amount of methylcyclopropene required to treat a normal room is about one gram or less. The recommended dosage is around 500–700 ppb for 4–6 hours at room temperature for a few crops.

A molecular encapsulation agent is a compound that has a lock and key structure similar to an enzyme whereby a substrate selectively fits into the encapsulation site.

The most preferred molecular encapsulation agent found to date is alpha-cyclodextrin. Other molecular encapsulation agents, such as crown ethers, polyoxyalkylenes, prophorines, polysiloxanes, phophazenes and zeolites, were also found to work. Most of these molecular encapsulation agents can be obtained from the Aldrich Chemical Company.

Methylcyclopropene can be complexed with cyclodextrin in water. For example, when the water is removed after methylcyclopropene is bubbled through an aqueous solution of alpha-cyclodextrin, it was discovered that the methylcyclopropene was firmly locked into the cyclodextrin cage structure. In addition, the cyclodextrin cake after drying can be milled into a powder and blended to a uniform concentration. It has been surprisingly discovered that this particular complex (methylcyclopropene and alpha-cyclodextrin) was stable for over one year as judged by accelerated shelf life studies. Moreover, a powdered complex can be easily measured and packaged into appropriately-sized doses for treatment of plants.

The method of delivery of the present invention provides a user-friendly application. It also promotes a lower initial dose of active compound and a decrease in the need for repeated applications as compared with previously proposed solid carrier systems.

A variety of molecular encapsulation agents may be utilized in the present invention provided they have the correct cage structure to form a molecular trap for the compound capable of inhibiting the ethylene response in plants. Thus, as one skilled in the art would recognize, the use of other molecular encapsulation agents falls within the spirit and scope of the present invention.

Cyclodextrins, also known as "Schardinger Dextrins", are cyclic oligosaccharides composed of glucose units bonded together by alpha 1,4 bonds. The six-membered ring structure is named alpha-cyclodextrin, the seven membered ring is beta-cyclodextrin and the eight membered ring is gamma-cyclodextrin. Generally, compounds that are encapsulated fit inside of the oligosaccharide ring.

As is well known, cyclodextrins are produced from starch of any selected plant variety such as corn, potato, waxy maize and the like. The starch may be modified or unmodified starch derived from cereal or tuber origin and the amylose or amylopectin fractions thereof. The selected starch in aqueous slurry at selected concentration up to about 35% by weight solids is usually liquefied as by gelatinization or treatment with liquefying enzyme such as bacterial alpha-amylase enzymes and then subjected to treatment with a cyclodextrin glucosyl transferase enzyme to form the cyclodextrin.

The amount of the individual alpha, beta and gamma cyclodextrins produced by treating the starch with the glucosyl transferase enzyme will vary depending on the selected starch, selected glucosyl transferace enzyme and processing conditions. The parameters to select for glucosyl transferase enzyme conversion for the desired result in the amount of each individual cyclodextrin to be produced is conventional and well described in the literature. Separation and purification of the cyclodextrin thus obtained is also conventional and well known to those of skill in the art.

In one embodiment, the cyclodextrin utilized in the complex of the present invention is alpha-cyclodextrin. However, as one skilled in the art will appreciate, any cyclodextrin or mixture of cyclodextrins, cyclodextrin polymers as well as modified cyclodextrins can also be utilized pursuant to the present invention. Cyclodextrins are available from American Maize Products Company, Hammond, Ind., as well as other vendors.

In order to form a molecular encapsulation agent complex, the active compound and the molecular encapsulation agent molecules are mixed together in a solution for a period of time sufficient to form the complex. The complex is then removed from the solution and dried. The dried complex is then ready for use.

As noted previously, the resulting complex of the present invention provides a number of advantages to manufacturers as well as ultimate consumers. Due to the ability of the cyclodextrin to entrap a large amount of cyclopropene, the present invention should lower the initial dosage of cyclopropene needed for treatment as compared with previously proposed solid carriers. Likewise, it should decease the need for repeated treatments of cyclopropene compared with previously proposed solid carriers. The potential of these advantages is demonstrated in the examples below which show the unexpected ability of the complex of the present invention to entrap large quantities of cyclopropene.

A still further advantage of the present invention is the increased stability of the resulting methylcyclopropene/alpha-cyclodextrin complex as compared to compressed gas. Based on heat stability testing, it was determined that when concentrated methylcyclopropene gas was exposed to heat of about 50° C., a 75% to 100% reduction in concentration was observed. When left at room temperature, the concentrated gas lost 30% to 42% of its concentration. On the other hand, when the methylcyclopropene/alpha-cyclodexrin complex of the present invention was exposed to 50° C., only a 38% reduction in the concentration of methylcyclopropene was observed. When left at room temperature, there was no reduction in the concentration of methylcyclopropene from the methylcyclopropene/alpha-cyclodextrin complex.

The present invention also provides a convenient product for commercial use. For example, select quantities of the complex of the present invention can be sealed into a package for retail and wholesale use. In one embodiment, the preferable package is made of polyvinyl alcohol. The inventors have discovered that polyvinyl alcohol increases the efficiency of release, reduces any exposure, and insures proper dosage. When the consumer is ready to use the complex, the consumer may either dissolve the powder in an aqueous solution (e.g., water) and expose the resulting solution to the plant.

Understandably, various changes and modifications to the presently preferred embodiments described herein will be apparent to those skilled in the art. Such changes and modifications can be made without departing from the spirit and scope of the present invention and without diminishing its intended advantages. Therefore, the claims are intended to cover such changes and modifications.

The Controlled Release of Compounds Capable of Inhibiting the Ethylene Response in Plants Controlled release of methylcyclopropene as well as other compounds capable of inhibiting the ethylene response in plants from a molecular encapsulation agent complex such as cyclodextrin is facilitated by the addition of an excess of water. Addition of an acid or alkaline substance to the water also facilitates a faster release of the active compound. Heating the water also facilitates a faster release of the active compound. Because methylcyclopropene has a high vapor pressure at normal working temperatures from 4 to 25° C., it quickly escapes into the atmosphere. By releasing methylcyclopropene from a complex in water in a closed container or room, the methylcyclopropene diffuses onto the ethylene receptor sites of all the plants within the room. Use of fans or other means to move the air for more suitable equilibration in the chamber is also often useful. Depending on the plant, generally a dose of less than 1 ppm (part per million) or preferably less than 500 ppb (parts per billion) of methylcyclopropene or some other active compound in the atmosphere of the sealed container or room for about 2–6 hours is sufficient to protect the plant or plant product from further ethylene damage.

The Plants Applicable to the Present Invention

The term "plant" is used generically in the present invention to also include woody-stemmed plants in addition to field crops, potted plants, cut flowers, harvested fruits and vegetables and ornamentals. Some of the plants that can be treated by the methods of the present invention are listed below.

Plants treated by the compounds of the present invention that inhibit the ethylene response need to be treated at levels that are below phytotoxic levels. This phytotoxic level varies not only by plant but also by cultivar.

When correctly used, the compounds of the present invention prevent numerous ethylene effects, many of which have been disclosed in U.S. Pat. Nos. 5,518,988 and 3,879,188, both of which are incorporated herein by reference in their entirety. The present invention can be employed to combat numerous plant ethylene responses. Ethylene responses may be initiated by either exogenous or endogenous sources of ethylene. Ethylene responses include, for example, (i) the ripening and/or senescence of flowers, fruits and vegetables, (ii) the abscission of foliage, flowers and fruit, (iii) the prolongation of the life of ornamentals, such as potted plants, cut flowers, shrubbery and dormant seedlings, (iv) the inhibition of growth in some plants such as the pea plant, and (v) the stimulation of plant growth in some plants such as the rice plant.

Vegetables which may be treated by the methods of the present invention to inhibit senescence include leafy green vegetables such as lettuce (e.g., *Lactuea sativa*), spinach (*Spinaca oleracea*) and cabbage (*Brassica oleracea;* various roots such as potatoes (*Solanum tuberosum*), carrots (Daucus); bulbs such as onions (Allium sp.); herbs such as basil (*Ocimum basilicum*), oregano (*Origanum vulgare*) and dill (*Anethum graveolens*); as well as soybean (*Glycine max*), lima beans (*Phaseolus limensis*), peas (Lathyrus sp.), corn (*Zea mays*), broccoli (*Brassica oleracea italica*), cauliflower (*Brassica oleracea botrytis*) and asparagus (*Asparagus officinalis*).

Fruits which may be treated by the methods of the present invention to inhibit ripening include tomatoes (*Lycopersicon esculentum*), apples (*Malus domes tica*), bananas (*Musa sapientum*), pears (*Pyrus communis*), papaya (*Carica papya*), mangoes (*Mangifera indica*), peaches (*Prunus persica*), apricots (*Prunus armeniaca*), nectarines (*Prunus persica nectarina*), oranges (Citrus sp.), lemons (*Citrus limonia*), limes (*Citrus aurantifolia*), grapefruit (*Citrus paradisi*), tangerines (*Citrus nobilis deliciosa*), kiwi (*Actinidia. chinenus*), melons such as cantaloupes (*C. cantalupensis*) and musk melons (*C. melo*), pineapples (*Aranae comosus*), persimmon (Diospyros sp.) and raspberries (e.g., *Fragaria* or *Rubus ursinus*), blueberries (Vaccinium sp.), green beans (*Phaseolus vulgaris*), members of the genus Cucumis such as cucumber (*C. sativus*) and avocados (*Persea americana*).

Ornamental plants which may be treated by the methods of the present invention to inhibit senescence and/or to prolong flower life and appearance (such as the delay of wilting), include potted ornamentals and cut flowers. Potted ornamentals and cut flowers which may be treated with the methods of the present invention include azalea (Rhododendron spp.), hydrangea (*Macrophylla hydrangea*), hibiscus (*Hibiscus rosasanensis*), snapdragons (Antirrhinum sp.), poinsettia (*Euphorbia pulcherima*), cactus (e.g., *Cactaceae schlumbergera truncata*), begonias (Begonia sp.), roses (Rosa sp.), tulips (Tulipa sp.), daffodils (Narcissus sp.), petunias (*Petunia hybrida*), carnation (*Dianthus caryophyllus*), lily (e.g., Lilium sp.), gladiolus (Gladiolus sp.), Alstroemeria (*Alstroemaria brasiliensis*), anemone (e.g., *Anemone bland*), columbine (Aquilegia sp.), aralia (e.g., *Aralia chinesis*), aster (e.g., *Aster carolinianus*), bougainvillea (Bougainvillea sp.), camellia (Camellia sp.), bellflower (Campanula sp.), cockscomb (Celosia sp.), falsecypress (Chamaecyparis sp.), chrysanthemum (Chrysanthemum sp.), clematis (Clematis sp.), cyclamen (Cyclamen sp.), freesia (e.g., *Freesia refracta*), and orchids of the family Orchidaceae.

Plants which may be treated by the methods of the present invention to inhibit abscission of foliage, flowers and fruit include cotton (Gossypium spp.), apples, pears, cherries (*Prunus avium*), pecans (*Carva illinoensis*), grapes (*Vitis vinifera*), olives (e.g., *Olea europaea*), coffee (*Cofffea arabica*), snapbeans (*Phaseolus vulgaris*), and weeping fig (*Ficus benjamina*), as well as dormant seedlings such as various fruit trees including apple, ornamental plants, shrubbery, and tree seedlings.

In addition, shrubbery which may be treated according to the present invention to inhibit abscission of foliage include privet (Ligustrum sp.), photinea (Photina sp.), holly (Ilex sp.), ferns of the family Polypodiaceae, schefflera (Schefflera sp.), aglaonema (Aglaonema sp.), cotoneaster (Cotoneastersp.), barberry (Berberris sp.), waxmyrtle (Myrica sp.), abelia (Abelia sp.), acacia (Acacia sp.), and bromeliades of the family Bromeliaceae.

EXAMPLES

While many of the examples described below are related to the synthesis molecular encapsulation agent compexing and delivery or application of methylcyclopropene to plants, the same synthesis methods have also been found effective for cyclopropene and other cyclopropene derivatives and the same molecular encapsulation agent compexing and delivery or application methods have also been found effective for cyclopropene, cyclopentadiene, diazocyclopentadiene and their derivatives. Methylcyclopropene was used in the examples because it is one of the most active derivatives of cyclopropene that binds to the ethylene receptor site of plants.

Example 1
Synthesis of Methylcyclopropene

At room temperature, nitrogen gas (99.95% pure) is pumped into a nitrogen vessel (35½"×28"×32") containing either sodium amide powder (90%-$NaNH_2$) or lithium diisopropylamide powder (97%-$[(CH_3)_2CH]_2NLi$). A separate powder addition vessel is also purged with the same nitrogen gas. Purging with nitrogen is necessary because of the reactivity of the above-mentioned Lewis bases with air, and to eliminate any contamination before conducting the synthesis reaction. In the powder addition vessel containing the inert atmosphere, the sodium amide (or an equivalent molar concentration of lithium diisopropylamide) is added in an amount ranging from 365–1100 grams, with the larger amount being preferred. To weigh the proper amount of the Lewis base, all weighing is performed in a nitrogen box with nitrogen purging to eliminate oxygen and the threat of spontaneous ignition of the base. Special care is important when working with such bases for proper safety.

Once the Lewis base in powder form is completely added, the openings in the powder addition vessel that were used for purging are sealed off to exclude air. The powder addition vessel is attached to the main system. The reaction vessel, which already has been purged with nitrogen and has been partially evacuated, is opened to the powder addition vessel to allow the powder to fall into the reaction vessel with the aid of nitrogen flow. Nitrogen enters the powder addition vessel during transfer of the Lewis base.

After the powder is transferred into the reaction vessel, the ball valve is closed. After the powder is added, a light mineral oil (dried with molecular sieves) or another equivalent solvent is added by opening the connecting ball valve and allowing it to pour into the reaction vessel with the aid of nitrogen flow. The amount of oil added during the reaction can vary from 1–47 liters, with the higher amount 47 liters being preferred. The reaction vessel is then purged and closed. The reaction vessel temperature is adjusted to a temperature anywhere from 0° C. to 75° C., and preferably about 20° C. to start the reaction. The temperature can be raised or lowered by heating or chilling the jacket using a circulating pump. Should the holding capacity of the vessel be exceeded, the procedure is repeated.

During the addition of ingredients, the contents of the reaction vessel are stirred with a propeller mixer, but splashing of the contents should be avoided. After mixing for 1–60 minutes, and preferably for about 20 minutes, 3-chloro-2-methylpropene is added to the reaction vessel in an amount ranging from 0.15–1.0 liters. During the addition of the 3-chloro-2-methylpropene, there is continuous purging with nitrogen gas. The liquid reactant 3-chloro-2-methylpropene is added slowly over a period of 20 minutes. During this addition, the temperature of the reaction vessel is monitored and kept at less than 40° C. Once the 3-chloro-2-methylpropene is completely added, the vessel should be agitated for an additional 1–30 minutes, and preferably for 15 minutes, using the propeller mixer discussed above. A reaction vessel pressure of about two atmospheres is used in this example.

After all the 3-chloro-2-methylpropene has been reacted, the desired end-product, methylcyclopropene, exists as a sodium salt. To react the remainder of the Lewis base and facilitate liberation of the methylcyclopropene product, the nitrogen purge is stopped and water is added ranging from 0.00–1.47 liters by adding the water under positive pressure over a period of 1 hour. Once all the water has been added, a ball valve connecting the vessel with the condenser is opened. Any pressure is then released by bubbling the gaseous methylcyclopropene product through a mixture of cyclodextrin dissolved in water (as explained later in this example).

Once the reactive ingredients have been mixed, the headspace gas in the reaction vessel is transferred to a 5 gallon mixing vessel, already lined with a bag filter (5–25 micron mesh plastic) and containing 0.9–2.8 kg of alpha-cyclodextrin, 0.575 liters of a buffer solution. The alpha-cyclodextrin is weighed out on an electronic scale and transferred to the mixing vessel by pouring it through the opening of the mixing vessel. The buffer solution is prepared by combining a 0.2 M sodium acetate solution with a 0.2 M acetic acid solution which gives a pH in the range of 3 to 5. The headspace gas in the reaction vessel is transferred by pulling a vacuum on the mixing vessel to 15 psi, closing the condenser/reaction vessel ball valve and opening the ball valve linking the condenser (15 coils, ⅜') to the mixing vessel, allowing the gas in the condenser, which has been chilled at a temperature of 0–10° C. by a chilling circulating pump, to pass through to the mixing vessel. The reason for chilling the gas in the condenser is to significantly reduce any 3-chloro-2-methylpropene from entering the mixing vessel. The lower boiling point of methylcyclopropene (which is approximately 12° C.) compared to the higher boiling point of the 3-chloro-2-methylpropene (which is 70° C.) prevents the later from entering the mixing vessel. The condenser is also positioned in such a way that the 3-chloro-2-methylpropene will return to the reaction flask.

Once the gas passes from the condenser, the condenser/mixing vessel ball valve is closed, and the condenser/reaction vessel ball valve is opened allowing the headspace gas from the reaction vessel to flow into the condenser. The condenser/reaction vessel ball valve is then closed, the condenser/mixing vessel ball valve is reopened, and the gas flows to the mixing vessel. Once the initial head space is transferred over to the mixing vessel, a vacuum will begin to be created in the reaction vessel which can be detected by reading the mounted pressure gauge. When this occurs, the reaction vessel is filled with nitrogen gas (99.95% pure) by closing any connections to the rest of the system, and allowing the nitrogen gas to enter through the nitrogen inlet valve when a slight vacuum occurs. Once the reaction vessel has been filled with nitrogen gas, which will be identifiable by reading the mounted pressure gauge, the head space gas from the reaction vessel is once again transferred to the mixing vessel. The process is repeated until the mixing vessel is filled with gas as indicated by the pressure gauge. A minimum concentration of 80,000 ppm of methylcyclopropene is preferred in the mixing vessel at this step. This concentration can be calculated the same way as previously mentioned. After the mixing vessel is filled, all the connections are closed, and the vessel is removed from the system and placed on a shaker, which is allowed to shake so that the mixture is completely agitated for 1–5 hours at less than 70° C. The methylcyclopropene is trapped in the alpha-cyclodextrin during this unit operation. After the contents are agitated, the mixing vessel is allowed to equilibrate for 0–72 hours, and preferably for at least 24 hours at a temperature of 0–30° C. (preferably about 4° C.). Next, the contents in the mixing vessel, if containing the buffer solution, are filtered out by vacuum filtration, by connecting a vacuum pump at the bottom outlet of the mixing vessel, which will remove the buffer solution from the mixture while the powder remains in the confines of the filtering bag.

Once all the buffer solution has been removed, the wet powder containing the entrapped methylcyclopropene is transferred onto a plastic tray and allowed to air dry for 24–48 hr. Once it has been dried, the filtered material is ground in a powder grinder, creating a fine powder (approximately 100 mm mesh). If the material in the mixing vessel did not contain the buffer solution, no filtering or grinding is needed. After the powder is ground, it is placed in a powder mill and allowed to mix for 5–10 minutes at approximately 100 rpm. Once the powder is mixed, it is analyzed and mixed with dextrose or dextrin to the desired concentration of methylcyclopropene entrapment. If the amount of entrapped methylcyclopropene is lower than the desired concentration, it is bulked and milled with other samples. In both cases, after the newly formed powders are mixed, they are analyzed again to insure that they meet specifications. Per every reaction vessel made, 2–7 mixing vessels can be filled, depending on the amount of methylcyclopropene remaining in the reaction vessel after the head space has been transferred. However, depending on the amount of methylcyclopropene gas remaining in the reaction vessel, a waiting period of 0–3 hours may be necessary for the reaction vessel to produce more methylcyclopropene gas. Once the mixing vessels are filled, and there is not enough methylcyclopropene gas to fill more vessels, the reaction vessel is removed from the system, but kept inside a hood.

Cleaning: Water is slowly added to the reaction vessel to begin the cleaning process. Water is added slowly due to its reactivity with excess sodium amide. When the sodium amide is mixed with water, ammonia and sodium salts are formed. Once the reaction vessel has been washed completely, it is allowed to air dry completely before it is reused. The three addition vessels are cleaned once a week with water. They are thoroughly rinsed with water until no reactants are found. All the piping/tubing and condenser are also cleaned thoroughly once a week with water. The mixing vessels and inner filter linings are thoroughly washed with water after every use. All waste water is disposed of according to governmental regulations. Cleanliness, in addition to purging of the vessels with nitrogen gas and the cooling of gas in the condenser are safety steps that also prevent any contamination of the methylcyclopropene.

Example 2
Manufacture of Methylcyclopropene Using 3-bromo-2-methylpropene and Lithium Diisopropylamide Under a nitrogen atmosphere, approximately 0.1 to 0.5 moles of lithium diisopropylamide are placed into a two liter container. 100 ml of a non-volatile organic solvent, such as dried mineral oil, is then added to the container. Approximately 0.1 to 0.5 moles of 3-bromo-2-methyl propene is then added to the container. A 1:1 molar ratio of the lithium amide and the halogenated methyl propene is utilized. The exothermic solution is then allowed to react until no heat was given off. Then, approximately 0.1 to 0.5 moles of a polar solvent, such as water, is added to the container.

The head space of the reaction is displaced with a syringe or by sweeping with nitrogen through a condenser and cold trap, connected to a vacuum system into a flask containing approximately 50 to 200 grams of alpha-cyclodextrin and 50 to 200 ml of water buffered at a pH of approximately 4 to 6. The cold trap is kept at a temperature of approximately 0–10° C., whereas the condenser is at a temperature ranging from approximately 10–20° C. This solution is then stirred for about 1 to 24 hours at a temperature ranging from room temperature to 45° C. Lastly, after the solution has reacted, the excess water is filtered out. Then the slurry is dried to a powder form. In this manner, a complex is formed in accordance with the present invention.

Plants are preferably exposed to a non-phytotoxic amount of the active compound. In one embodiment, approximately 0.1 gram of an encapsulated cyclopropene or derivative thereof per 50 to 500 cubic feet of atmosphere to be treated is dissolved in an aqueous solution and exposed to plants to prolong their life or inhibit their ethylene response.

The methods of the present invention involve initially the step of providing the complex of the present invention. Then the complex is dissolved to release the gaseous form of the complex. A variety of solutions may be utilized and generally encompass polar solvents, such as water, DMSO, ethanol and methanol. To expose the plant to the gaseous cyclopropene or derivative thereof, the aqueous solution is preferably positioned near the plant. Alternatively, the powder may be placed in an aerosol can containing sufficient water and 40–50 psi of compressed gas. Then, the gaseous cyclopropene may be sprayed onto the plant.

Example 3
Release of Methylcyclopropene from Cyclodextrin

To release methylcyclopropene from the cyclodextrin molecular encapsulation agent and treat plants, the first thing that should be done is to place the plants into a closed environment, preferably at elevated temperatures, preferably from 13° to 24° C. The amount of methylcyclopropene should preferably be from 100 to 500 ppb (parts per billion of methylcyclopropene in the atmosphere after release) for crops like carnations. The amount of molecular encapsulating agent complex needed to release the proper amount of methylcyclopropene or any other compound capable of inhibiting the ethylene response in plants will depend upon the plant being treated and the specific complex formulation used. Before the active compound is released, the treating chamber is closed and the air flow arranged so that all the plants in the closed chamber will be treated. The methylcyclopropene/alpha-cyclodextrin complex is then added to water. The amount of water used should be at least 10 times the weight of the cyclodextrin and preferably 100 times the weight of the cyclodextrin. Other factors that facilitate a more complete release of the active compound capable of inhibiting the ethylene response in plants are the addition of an acidic or alkaline agent to the water so as to buffer the water to an acidic or basic pH. Additionally, the water containing the cyclodextrin complex can be heated up to 45° C. to facilitate a better release of the methylcyclopropene. The release of methylcyclopropene is faster with heating or changing pH, but in lieu of these treatments, use of a greater amount of water is sufficient to obtain a full release of the methylcyclopropene from the cyclodextrin complex. The plant treatment time is usually at least one hour, but preferably at least 6 hours unless the plants are being held at a temperature less than 15° C. in which case more time is preferred (sometimes as much as 10 hours). Once the plants are treated, the sealed chamber may be opened if desired. The methylcyclopropene is now protecting the plants because it has blocked all the available ethylene receptor sites. This treatment will protect the plants from the action of ethylene until the plant grows new unblocked ethylene receptor sites.

Example 4
Comparative Experiments

The following comparative examples demonstrate the effectiveness of the molecular encapsulation agent complexes of the present invention.

The comparative examples demonstrate the benefits of the present invention (utilizing an alpha-cyclodextrin/methylcyclopropene complex) as compared to traditional solid inert carriers, such as wood flour and molecular sieves. Specifically, these comparative examples demonstrate the amount of methylcyclopropene absorbed by traditional solid carriers as compared to that entrapped by utilizing a molecular encapsulation agent, alpha-cyclodextrin, of the present invention.

The Wood Flour Comparative Example

This experiment evaluates the differences between utilizing the complex of the present invention with a solid carrier, as proposed in U.S. Pat. No. 5,518,988. Specifically, the inventors tested the absorption amount, if any, of methylcyclopropene onto wood flour. The wood flour used was obtained from American Wood Fibers and was identified as #10010 Hardwood.

To evaluate the amount of absorption of methylcyclopropene, 0.01 grams of wood flour (previously exposed to methylcyclopropene in a buffered water solution as described below for the molecular sieve comparative example) was weighed out in a 25 ml vial, and dissolved with 5 ml of deionized water. Then, 1 ml of the headspace from the vial was injected into a gas chromatograph (a total of 20 ml of headspace was tested). In addition to testing with 0.01 grams of wood flour, 0.1 grams was also tested. Alpha-cyclodextrin was also tested under the same conditions. It was experimentally found that no methylcyclopropene attachment to the wood flour was detectable. This shows that use of a dry absorbent, such as wood flour, was not effective in absorbing methylcyclopropene.

The Molecular Sieve Comparative Example

To evaluate the differences between utilizing a molecular encapsulation agent complex of the present invention and molecular sieves, another comparative experiment was also conducted. Molecular sieves were selected for these comparison tests because they are one of the most common carriers of chemicals in the chemical industry.

Two types of molecular sieves were utilized in this comparative example, 13X and 5A. Both were obtained from the Aldrich Chemical Company in Milwaukee, Wis. Each molecular sieve was first dried at 50° C. for 30 minutes before being used. 25 grams of each were then placed in separate 250 ml Erlenmeyer flasks and cooled to −80° C. by placing then in a dry ice/acetone bath. 20 ml of methylcyclopropene (approximately 60,000 ppm) was injected into the flask and allowed to sit for 24 hours either at room temperature or at 4° C. 1 gram of molecular sieve was then weighed in a 20 ml vial, and 5 ml of deionized water was added to release the methylcyclopropene. 1 ml of the headspace from the vial was injected into a gas chromatograph to determine the concentration of methylcyclopropene adsorbed onto the molecular sieves. The following methylcyclopropene release data was obtained.

| Molecular Sieve/Condition | | Amount Released |
| --- | --- | --- |
| 13X | cooled to 4° C. for 24 hr. | 15 ppm |
| 13X | room temperature 24 hr. | 15 ppm |
| 5A | cooled to 4° C. for 24 hr. | None detected |
| 5A | room temperature 24 hr. | None detected |

The Alpha-Cyclodextrin Complex Comparative Example

The alpha-cyclodextrin/methylcyclopropene complex used in this example was made by trapping 80,000 ppm of methylcyclopropene in a 5 gallon mixing vessel with 1.3 kg of alpha-cyclodextrin in 0.575 liters of buffer solution having a pH of 4. The buffer solution was made with 0.2 M sodium acetate and 0.2 M acetic acid solutions. This is referred to as the "wet" cyclodextrin loading in the results discussed below. A "dry" cyclodextrin loading was also run. In the dry experiment, the methylcyclopropene was contacted with dry alpha-cyclodextrin, i.e., cyclodextrin that was not in an aqueous solution. In both experiments, the vessel was chilled to 4° C. and the contents mixed for 24 hours. Once the methylcyclopropene is trapped onto the cyclodextrin, the pressure fell from about 2 atmospheres to a vacuum. Nitrogen gas was then added to atmospheric pressure. The buffer solution was removed by filtering through a filtering bag within the vessel and the cyclodextrin cake was transferred to a plastic tray and allowed to air dry for 48 hours. The dry cyclodextrin with entrapped methylcyclopropene was ground with a powder grinder to a 100 mm mesh size. The complex was stored for two weeks before analysis.

To evaluate the amount of methylcyclopropene complexed or trapped by alpha-cyclodextrin, 0.01 grams of cyclodextrin (previously exposed to methylcyclopropene as described above) was weighed out in a 25 ml vial, and dissolved with 5 ml of deionized water. Then 1 ml of the headspace from the vial was injected into a gas chromatograph to determine the concentration of methylcyclopropene in the complex. The results are shown below. The methylcyclopropene was absorbed either wet or dry onto the cyclodextrin and then evaluated as described above.

| Cyclodextrin loading | Amount Released |
| --- | --- |
| water | 500–1000 ppm |
| dry | 200–500 ppm |

These results demonstrate that the 13X molecular sieve was only capable of taking up 15 ppm of methylcyclopropene. The heat of adsorption may have caused the decay of some methylcyclopropene according to the chromatographic results, but it is estimated that no more than 15 ppm could have been lost. In contrast, the results from the molecular encapsulation agent complex of the present invention demonstrate a substantially complete entrapment of the methylcyclopropene. These dramatic differences in release amounts of methylcyclopropene could not have been expected from the literature. Clearly, the molecular encapsulation agent complex of the present invention is far superior to the passive absorption to solids taught in U.S. Pat. No. 5,518,988.

What is claimed is:

1. A complex formed from a molecular encapsulation agent and a compound having the following structure $(R)_n\triangle$ wherein n is a number from 1 to 10 and R is selected from the group consisting of hydrogen, saturated or unsaturated C1 to C10 alkyl, hydroxy, halogen, C1 to C10 alkoxy, amino and carboxy.

2. The complex of claim 1 wherein the molecular encapsulation agent is selected from the group consisting of a cyclodextrin, a crown ether, a polyoxyalkylene, a prophorine, a polysiloxane, a phophazene and a zeolite.

3. The complex of claim 1 wherein the compound is selected from the group consisting of cyclopropene and dimethylcyclopropene.

4. The complex of claim 1 wherein the molecular encapsulation agent is cyclodextrin.

5. The complex of claim 4 wherein the cyclodextrin is alpha-cyclodextrin.

6. A method of delivering a compound to a plant to inhibit an ethylene response in the plant, the method comprising the step of contacting a complex formed from a molecular encapsulation agent and a compound having the following structure $(R)_n\triangle$ wherein n is a number from 1 to 10 and R is selected from the group consisting of hydrogen, saturated or unsaturated C1 to C10 alkyl, hydroxy, halogen, C1 to C10 alkoxy, amino and carboxy, with a solvent capable of dissolving the molecular encapsulation agent, and thereby liberating the compound from the molecular encapsulation agent so that it can contact the plant.

7. The method of claim 6 wherein the molecular encapsulation agent is selected from the group consisting of a cyclodextrin, a crown ether, a polyoxyalkylene, a prophorine, a polysiloxane, a phophazene and a zeolite.

8. The method of claim 6 wherein the compound is selected from the group consisting of cyclopropene and dimethylcyclopropene.

9. The method of claim 6 wherein the molecular encapsulation agent is cyclodextrin.

10. The method of claim 9 wherein the cyclodextrin is alpha-cyclodextrin.

11. The method of claim 6 wherein the solvent comprises water.

12. The method of claim 11 wherein the water additionally comprises an acidic or alkaline agent.

13. The method of claim 6 further comprising bubbling a gas through the solvent while it is in contact with the complex.

14. The method of claim 6 further comprising applying heat to the solvent either before it contacts the complex or during that contact.

15. The complex of claim 1 wherein n is a number from 5–10 and R is selected from the group consisting of hydrogen, saturated or unsaturated C5 to C10 alkyl, hydroxy, halogen, C5 to C10 alkoxy, amino and carboxy.

16. The complex of claim 15 wherein the molecular encapsulation agent is selected from the group consisting of a cyclodextrin, a crown ether, a polyoxyalkylene, a prophorine, a polysiloxane, a phosphazene and a zeolite.

17. The complex of claim 15 wherein the compound is selected from the group consisting of cyclopropene and dimethylcyclopropene.

18. The complex of claim 15 wherein the molecular encapusulation agent is cyclodextrin.

19. The complex of claim 18 wherein the cyclodextrin is alpha-cyclodextrin.

* * * * *